United States Patent
Cordi et al.

(10) Patent No.: US 8,288,433 B2
(45) Date of Patent: Oct. 16, 2012

(54) DIAZENIUMDIOLATE COMPOUNDS, A PROCESS FOR THEIR PREPARATION AND PHARMACEUTICAL COMPOSITIONS CONTAINING THEM

(75) Inventors: Alexis Cordi, Suresnes (FR); Laure Haberkorn, Bois-Colombes (FR); Tony Verbeuren, Vernouillet (FR); Christine Courchay, Igny (FR); Serge Simonet, Conflans ste Honorine (FR)

(73) Assignee: Les Laboratoires Servier, Suresnes Cedex (FR)

( * ) Notice: Subject to any disclaimer, the term of this patent is extended or adjusted under 35 U.S.C. 154(b) by 176 days.

(21) Appl. No.: 12/735,048

(22) PCT Filed: Dec. 10, 2008

(86) PCT No.: PCT/FR2008/001716
§ 371 (c)(1),
(2), (4) Date: Jun. 10, 2010

(87) PCT Pub. No.: WO2009/103875
PCT Pub. Date: Aug. 27, 2009

(65) Prior Publication Data
US 2010/0286225 A1    Nov. 11, 2010

(30) Foreign Application Priority Data
Dec. 11, 2007  (FR) .................... 07 08604

(51) Int. Cl.
*A61K 31/404* (2006.01)
*C07D 209/04* (2006.01)
(52) U.S. Cl. ....................... 514/415; 548/483
(58) Field of Classification Search ............ 548/483
See application file for complete search history.

(56) References Cited

U.S. PATENT DOCUMENTS
3,565,911 A    2/1971    Beregi et al.

FOREIGN PATENT DOCUMENTS

| FR | 2003311 | 11/1969 |
| JP | 58124766 | 7/1983 |
| JP | 07118231 | 5/1995 |
| JP | 7118231 | 5/1995 |
| WO | WO98/19996 | 5/1998 |
| WO | WO 98/19996 | 5/1998 |

OTHER PUBLICATIONS

International Search Report for PCT/FR2008/001716 of July 13, 2009.
Konter, J, et al., "Synthesis of diazen-1-ium-1,2-diolates monitored by the NOTIZER apparatus" european journal of organic chemistry, vol. 4, p. 616-624, 2007.
Liu D-G, et al., "Acylsulfonamide-containign PTP1B inhibitors designed to mimic and enzyme-bound water of hydration" Bioorganic and Medicinal Chemistry Letters, vol. 13, No. 18, p. 3005-2007, 2003.
Saavedram J., et al., "piperazine as a linker for incorporating the nitric oxide-releasing diazeniumdiolate group into other biomedically relevant functional molecules" Journal of Organich Chemistry, vol. 64, No. 14, p. 5124-5131, 1999.

*Primary Examiner* — Shawquia Young
(74) *Attorney, Agent, or Firm* — Hueschen and Sage

(57) ABSTRACT

Compounds of formula (I):

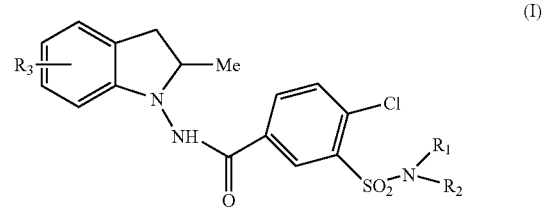

wherein:
$R_1$ represents a hydrogen atom or a —COOR group,
$R_2$ represents a group G or a linear or branched ($C_1$-$C_6$)alkyl group substituted by a group G, wherein G represents a —$(CH_2)_n$-A-$(CH_2)_m$—B—$(CR_4R_5)_p$—$(CH_2)_o$—$R_6$ group as defined in the description,
$R_3$ represents a hydrogen atom, an alkyl group or an $NO_2$ group.
Medicinal products containing the same which are useful in treating hypertension and cardiovascular pathologies.

14 Claims, No Drawings

DIAZENIUMDIOLATE COMPOUNDS, A PROCESS FOR THEIR PREPARATION AND PHARMACEUTICAL COMPOSITIONS CONTAINING THEM

The present invention relates to new diazeniumdiolate compounds, to a process for their preparation and to pharmaceutical compositions containing them.

Those compounds have novel structures and may be used in the field of hypertension and cardiovascular disease.

Hypertension brings about an increased risk of vascular accidents, especially at the cerebral and coronary level. It is more and more frequently associated with other pathologies such as atherosclerosis or metabolic disorders such as obesity, diabetes or renal insufficiency, which appreciably increases the risk of spasms and thromboses.

Diuretics represent a class of very effective anti-hypertensive medicaments. Their main effect is to reduce the total peripheral resistance by increasing the excretion of sodium and decreasing plasma volume. Diuretics reduce the number of cardiovascular accidents and are also effective in cardiac insufficiency. They also have the advantage of having few contra-indications and of being well tolerated. They may be combined with other classes of anti-hypertensives and are systematically included when a bi- or tri-therapy is required.

Since the discovery of its cardiovascular action in 1980, nitrogen monoxide (NO) has been recognised as a vasodilatory and vasoprotective molecule capable of preventing vasospasms, atherosclerosis and thrombosis, that endogenous mediator thus offering protection against cardiovascular disease. NO is essentially produced by the endothelial cells and, in cardiovascular pathologies, dysfunction of the endothelium causes a deficiency in endogenous NO.

Nitrovasodilator compounds, such as nitroglycerine, have been used for a long time to treat angina pectoris and cardiac insufficiency. The beneficial effect of those products is associated with their capacity to form NO (spontaneously or metabolically). Their use has also led to the observation that in the hypertensive patient those NO donors cause a substantial reduction in systolic arterial pressure. Uncontrolled systolic arterial pressure is a significant risk factor for cerebral and cardiac accidents and is often resistant to anti-hypertensive treatments. Indeed, despite the demonstrated anti-hypertensive and vasoprotective effects of diuretics and other classes of anti-hypertensive products, arterial pressure, especially systolic, remains difficult to control, and the morbidity and mortality rates remain high.

The addition of an NO-donor property to diuretic products would improve their anti-hypertensive, cardioprotective and vasculoprotective properties and would add a direct anti-thrombotic action, NO having a platelet anti-aggregating and anti-thrombotic effect (Walford G. et al., 2003, J. Thromb. Haemost., 1, 2112-2118).

In addition to having a novel structure, the compounds of the present invention exhibit such a dual pharmacological activity, conferring upon them entirely surprising and valuable properties in the field of hypertension and cardiovascular pathologies.

More specifically, the present invention relates to compounds of formula (I):

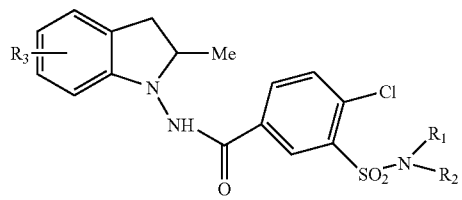

(I)

wherein:
$R_1$ represents a hydrogen atom or a —COOR group wherein R represents a linear or branched ($C_1$-$C_6$)alkyl group or an aryl-($C_1$-$C_6$)alkyl group in which the alkyl moiety may be linear or branched, $R_2$ represents a group G or a linear or branched ($C_1$-$C_6$)alkyl group substituted by a group G, wherein G represents a —$(CH_2)_n$-A-$(CH_2)_m$—B—$(CR_4R_5)_p$—$(CH_2)_o$—$R_6$ group wherein:
n is 0, 1, 2 or 3,
m is 0, 1, 2 or 3,
p is 0 or 1,
o is 0, 1 or 2,
$R_4$ and $R_5$, which may be identical or different, each represent a hydrogen atom or a linear or branched ($C_1$-$C_6$) alkyl group,
wherein one of the groups —$CH_2$— or —$CR_4R_5$— of the G chain may equally be replaced, if desired, by a phenylene, —PhC(O)— or —PhC(O)O— group (wherein Ph denotes phenyl),
A and B, which may be identical or different, each represent a bond, —NH— or a group:

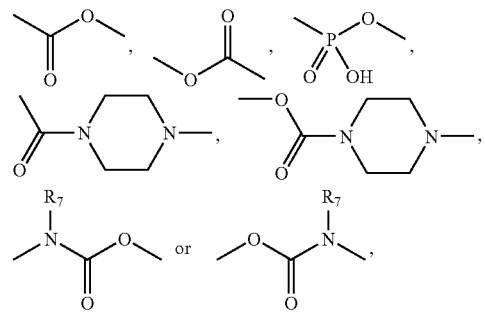

wherein $R_7$ represents a hydrogen atom or a linear or branched ($C_1$-$C_6$)alkyl group,
and $R_6$ represents a group

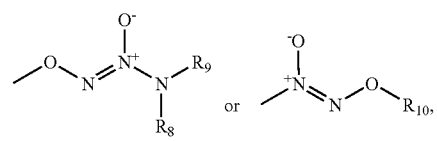

wherein $R_8$, $R_9$ and $R_{10}$, which may be identical or different, each represent a hydrogen atom or a linear or branched ($C_1$-$C_6$)alkyl group unsubstituted or substituted by an amino group, or $R_8$ and $R_9$ together form a linear or branched ($C_1$-$C_6$)alkylene chain,
$R_3$ represents a hydrogen atom, a linear or branched ($C_1$-$C_6$) alkyl group or an $NO_2$ group,
to their enantiomers and diastereoisomers and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine, tert.-butylamine etc.

More especially, the invention relates to compounds of formula (I) wherein $R_1$ represents a hydrogen atom.

Advantageously, the invention relates to compounds of formula (I) wherein $R_3$ represents a hydrogen atom or an $NO_2$ group.

$R_2$ advantageously represents a group:

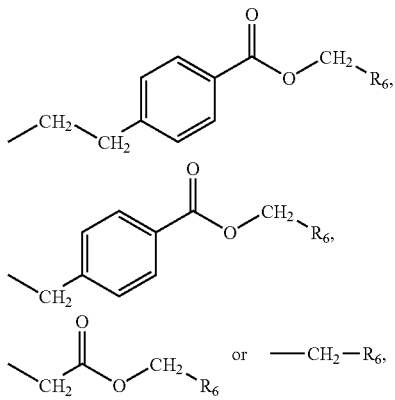

wherein $R_6$ is as defined hereinbefore.

The preferred $R_6$ group according to the invention is the group —O—N=N(O)—$NR_8R_9$.

The bond —N=N— of the $R_6$ group preferably has the Z configuration.

$R_8$ and $R_9$ preferably represent a linear ($C_1$-$C_6$)alkyl group, such as, for example, an ethyl group.

Even more especially, the invention relates to the following compounds of formula (I):

({[(1Z)-2,2-diethyl-1-oxidohydrazono]amino}oxy)methyl 3-{[({2-chloro-5-[(2-methyl-5-nitro-2,3-dihydro-1H-indol-1-yl)carbamoyl]phenyl}sulphonyl)amino]methyl}benzoate, ({[(1Z)-2,2-diethyl-1-oxidohydrazono]amino}oxy)methyl 3-{[({2-chloro-5-[(2-methyl-2,3-dihydro-1H-indol-1-yl)carbamoyl]phenyl}sulphonyl)amino]methyl}benzoate, tert-butyl({2-chloro-5-[(2-methyl-2,3-dihydro-1H-indol-1-yl)carbamoyl]phenyl}-sulphonyl)[({[(1Z)-2,2-diethyl-1-oxidohydrazono]amino}oxy)methyl]carbamate, ({[(1Z)-2,2-diethyl-1-oxidohydrazono]amino}oxy)methyl N-(tert-butoxycarbonyl)-N-({2-chloro-5-[(2-methyl-2,3-dihydro-1H-indol-1-yl)carbamoyl]phenyl}-sulphonyl)glycinate, ({[(1Z)-2,2-diethyl-1-oxidohydrazono]amino}oxy)methyl N-({2-chloro-5-[(2-methyl-2,3-dihydro-1H-indol-1-yl)carbamoyl]phenyl}sulphonyl)glycinate, ({[(1Z)-2,2-diethyl-1-oxidohydrazono]amino}oxy)methyl 4-{[({2-chloro-5-[(2-methyl-2,3-dihydro-1H-indol-1-yl)carbamoyl]phenyl}sulphonyl)amino]-methyl}benzoate, ({[(1Z)-2,2-diethyl-1-oxidohydrazono]amino}oxy)methyl 4-({[(2-chloro-5-{[(2R)-2-methyl-2,3-dihydro-1H-indol-1-yl]carbamoyl}phenyl)sulphonyl]amino}-methyl)benzoate, ({[(1Z)-2,2-diethyl-1-oxidohydrazono]amino}oxy)methyl 4-({2-[({2-chloro-5-[(2-methyl-2,3-dihydro-1H-indol-1-yl)carbamoyl]phenyl}sulphonyl)amino]ethyl})-benzoate, ({[(1Z)-2,2-diethyl-1-oxidohydrazono]amino}oxy)methyl 4-{2-[({2-chloro-5-[((2R)-2-methyl-2,3-dihydro-1H-indol-1-yl)carbamoyl]phenyl}sulphonyl)-amino]ethyl}benzoate.

The invention relates also to a process for the preparation of the compounds of formula (I) which is characterised in that there is used as starting material a compound of formula (II):

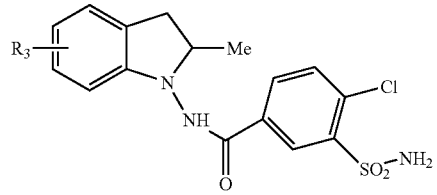

wherein $R_3$ is as defined for formula (I),
which is condensed with a compound of formula (III):

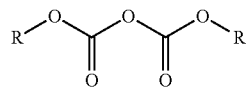

wherein R is as defined for formula (I),
to yield a compound of formula (IV):

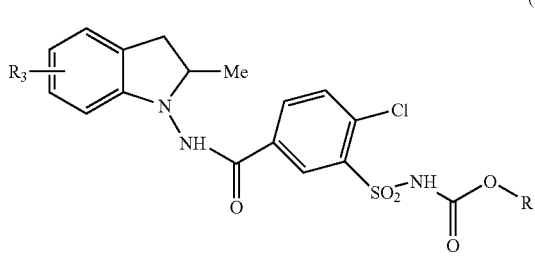

wherein $R_3$ and R are as defined hereinbefore,
which is condensed, in the presence of a base, with a compound of formula (V):

$$X—R_2 \quad (V)$$

wherein $R_2$ is as defined for formula (I) and X represents a halogen atom,
to yield a compound of formula (I/a), a particular case of the compounds of formula (I):

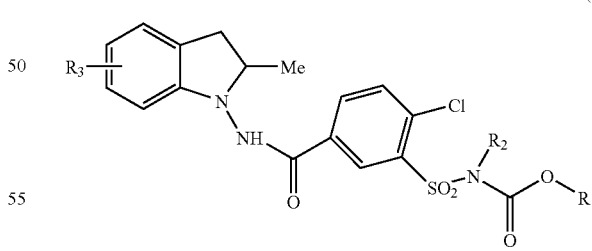

wherein R, $R_2$ and $R_3$ are as defined for formula (I),
it being possible for the compounds of formula (I/a) to be obtained also by condensation of a compound of formula Cl—$(CH_2)_o$—$R_6$, wherein o and $R_6$ are as defined for formula (I), with a carboxylic or phosphoramidic function present in the group G,
which compounds of formula (I/a) are optionally heated in acid medium to yield a compound of formula (I/b), a particular case of the compounds of formula (I):

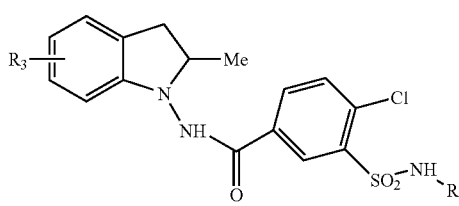

(I/b)

wherein $R_2$ and $R_3$ are as defined for formula (I),
which compounds of formulae (I/a) and (I/b), the totality of which constitutes the compounds of formula (I), are purified, where appropriate, according to a conventional purification technique, are optionally separated into isomers according to a conventional separation technique and are converted, if desired, into addition salts with a pharmaceutically acceptable acid or base.

The compounds of formula (II) as defined hereinbefore are obtained by conventional reactions of organic chemistry, such as, for example, the process described in patent specification FR 2 003 311.

Given their pharmacological properties; the compounds of the present invention are of use in the treatment of hypertension and cardiovascular pathologies and complications thereof, such as retinopathy, cerebral accidents, dementia, left ventricular hypertrophy, cardiac insufficiency, angina pectoris, myocardial infarction and nephropathy. The compounds according to the invention are also of use in cardiovascular pathologies associated with atherothrombosis, such as cerebral and coronary accidents, arteritis and vasculopathies, as well as in vascular complications of a number of disorders, such as diabetes, obesity, metabolic syndrome, cancer, fibrosis of the liver etc. The compounds are also of use in hypertension of pulmonary, ocular or portal origin.

The present invention relates also to pharmaceutical compositions comprising as active ingredient at least one compound of formula (I), an optical isomer thereof, or an addition salt thereof with a pharmaceutically acceptable acid or base, alone or in combination with one or more pharmaceutically acceptable, inert, non-toxic excipients or carriers.

Among the pharmaceutical compositions according to the invention there may be mentioned more especially those which are suitable for oral, parenteral (intravenous, intramuscular or subcutaneous), per- or trans-cutaneous, intravaginal, rectal, nasal, perlingual, buccal, ocular or respiratory administration.

The pharmaceutical compositions according to the invention for parenteral injections include especially sterile aqueous and non-aqueous solutions, dispersions, suspensions and emulsions, as well as sterile powders for the reconstitution of injectable solutions or dispersions.

The pharmaceutical compositions according to the invention for solid oral administration include especially tablets or dragées, sublingual tablets, sachets, capsules and granules and, for liquid oral, nasal, buccal or ocular administration, they include especially emulsions, solutions, suspensions, drops, syrups and aerosols.

The pharmaceutical compositions for rectal or vaginal administration are preferably suppositories, and those for per- or trans-cutaneous administration include especially powders, aerosols, creams, ointments, gels and patches.

The pharmaceutical compositions mentioned above illustrate the invention but do not limit it in any way.

Among the pharmaceutically acceptable, inert, non-toxic excipients or carriers there may be mentioned, by way of example and without implying any limitation, diluents, solvents, preservatives, wetting agents, emulsifiers, dispersants, binders, swelling agents, disintegrants, retardants, lubricants, absorbants, suspension agents, colourants, flavourings, etc.

The dosage used varies according to the age and weight of the patient, the administration route, the pharmaceutical composition employed, the nature and severity of the disorder, and the administration of any associated treatments. The dosage ranges from 0.1 mg to 1 g in one or more administrations per day.

The Examples which follow illustrate the invention but do not limit it in any way. The starting materials employed are known products or products prepared according to known procedures.

The structures of the compounds described in the Examples were determined according to the usual spectrophotometric techniques (infra-red, NMR, mass spectrometry . . . ).

The following Preparations lead to synthesis intermediates for use in the preparation of the compounds of the invention.

Intermediate 1

5-(Benzyloxy)-5-oxopentanoic Acid

Dissolve glutaric anhydride ($8.76 \times 10^{-2}$ mol) in dichloromethane (300 ml) and place under stirring. Add 4-dimethylaminopyridine ($7.88 \times 10^{-2}$ mol) and benzyl alcohol ($7.88 \times 10^{-2}$ mol) and then leave the reaction mixture at ambient temperature. After 4 hours and 30 minutes, the mixture is hydrolysed with aqueous 5% sodium carbonate solution (200 ml). Separate the two phases by decanting. The aqueous phase is then acidified with aqueous 1M hydrochloric acid solution and subsequently extracted with ethyl acetate. The organic phase is washed with brine, dried over magnesium sulphate, filtered and evaporated to dryness under reduced pressure.

The title product is obtained in the form of a white solid which is used without subsequent purification.

Intermediate 2

Benzyl Chloromethyl Pentanedioate

Dissolve intermediate 1 ($2.24 \times 10^{-2}$ mol) in dichloromethane (75 ml), add water (75 ml) and then cool to 0° C. while stirring vigorously. Subsequently, add sodium hydrogen carbonate ($8.91 \times 10^{-2}$ mol) and tetrabutylammonium sulphate ($2.24 \times 10^{-3}$ mol). After 15 minutes, add dropwise a solution of chloromethyl chlorosulphate ($2.70 \times 10^{-2}$ mol) in dichloromethane (20 ml). Stir the reaction mixture vigorously at 0° C. for 1 hour and then allow to return to ambient temperature. After 1 hour and 30 minutes, the two phases are separated by decanting. The organic phase is washed with brine, dried over magnesium sulphate, filtered and then evaporated to dryness under reduced pressure.

The title product is obtained in the form of a colourless oil which is used without subsequent purification.

Intermediate 3

Benzyl Iodomethyl Pentanedioate

Dissolve sodium iodide ($2.70 \times 10^{-2}$ mol) in acetone (100 ml). Place under stirring and then add a solution of intermediate 2 ($2.25 \times 10^{-2}$ mol) in acetone (40 ml). Heat the reaction mixture at 45° C. After 48 hours, the reaction mixture is filtered. The solid residue is rinsed with acetone and then the filtrate is evaporated to dryness under reduced pressure.

The title product is obtained in the form of a viscous brown residue which is used without subsequent purification.

Intermediate 4

4-(Benzyloxy)-4-oxobutanoic Acid

Dissolve succinic anhydride (0.10 mol) in dichloromethane (300 ml) and place under stirring. Add 4-dimethylaminopyridine ($8.3 \times 10^{-2}$ mol) and benzyl alcohol ($8.3 \times 10^{-2}$ mol) and then leave the reaction mixture at ambient temperature. After 1 hour and 30 minutes, the mixture is hydrolysed with an aqueous 5% sodium carbonate solution (200 ml). Separate the two phases by decanting. The aqueous phase is then acidified with an aqueous 1M hydrochloric acid solution and subsequently extracted with ethyl acetate. The organic phase is washed with brine, dried over magnesium sulphate, filtered and evaporated to dryness under reduced pressure.

The title product is obtained in the form of a white solid which is used without subsequent purification.

Intermediate 5

Benzyl Chloromethyl Butanedioate

Dissolve intermediate 4 ($4.80 \times 10^{-3}$ mol) in dichloromethane (15 ml), add water (15 ml) and then cool to 0° C. while stirring vigorously. Subsequently, add sodium hydrogen carbonate ($1.90 \times 10^{-2}$ mol) and tetrabutylammonium sulphate ($4.80 \times 10^{-4}$ mol). After 15 minutes, add dropwise a solution of chloromethyl chlorosulphate ($5.76 \times 10^{-3}$ mol) in dichloromethane (4 ml). Stir the reaction mixture vigorously at 0° C. for one hour and then allow to return to ambient temperature. After 5 hours and 30 minutes, the two phases are separated by decanting. The organic phase is washed with brine, dried over magnesium sulphate, filtered and then evaporated to dryness under reduced pressure. The colourless oily crude product is chromatographed on a silica column using as eluant an 80/20 n-heptane/ethyl acetate mixture.

The title product is obtained in the form of a colourless oil.

Intermediate 6

Benzyl Iodomethyl Butanedioate

Dissolve sodium iodide ($4.67 \times 10^{-3}$ mol) in acetone (18 ml). Place under stirring and then add a solution of intermediate 5 ($3.89 \times 10^{-3}$ mol) in acetone (7.5 ml). Heat the reaction mixture at 45° C. After 6 hours, the reaction mixture is filtered. The solid residue is rinsed with acetone and then the filtrate is evaporated to dryness under reduced pressure.

The title product is obtained in the form of a viscous brown residue which is used without subsequent purification.

Intermediate 7

Methyl 2-(bromomethyl)benzoate

Dissolve methyl 2-methylbenzoate ($3.33 \times 10^{-2}$ mol) in chloroform (30 ml). Add N-bromosuccinimide ($3.50 \times 10^{-2}$ mol), 2,2'-azobis(2-methylpropionitrile) ($3.65 \times 10^{-4}$ mol) and heat progressively to 65° C. to allow initiation of the free-radical reaction. Subsequently, reflux the reaction mixture for 5 hours. The mixture is then cooled to ambient temperature. Filter off the precipitate that has formed. Evaporate the filtrate to dryness under reduced pressure.

The title product is obtained in the form of an orange-coloured oil which is used without subsequent purification.

Intermediate 8

4-Chloro-N-[(2R)-2-methyl-2,3-dihydro-1H-indol-1-yl]-3-sulphamoyl benzamide

The title product is obtained by separation of 3-(aminosulphonyl)-4-chloro-N-(2-methyl-2,3-dihydro-1H-indol-1-yl) benzamide carried out by preparative chiral chromatography.

Intermediate 9

Methyl 4-(2-bromoethyl)benzoate

Suspend 4-(2-bromoethyl)benzoic acid ($1.31 \times 10^{-2}$ mol) in methanol (40 ml). Place the mixture under stirring, add sulphuric acid (1 ml) and heat at 60° C. After approximately 10 minutes, the mixture is perfectly clear. After heating for 2 hours, the reaction is terminated. Allow the mixture to return to ambient temperature and then pour it into water (100 ml). Extract with ethyl acetate (2×100 ml). The organic phase is washed with brine, dried over magnesium sulphate, filtered and then evaporated to dryness under reduced pressure.

The title product is obtained in the form of a colourless oil which is used without subsequent purification.

Intermediate 10

Methyl 4-(1-bromoethyl)benzoate

Dissolve 4-(1-bromoethyl)benzoic acid ($2.18 \times 10^{-3}$ mol) in methanol (12 ml). Place the mixture under stirring and then slowly add sulphuric acid (0.5 ml). After stirring for one night at ambient temperature, the reaction mixture is poured into water (50 ml). Extract with dichloromethane (3×30 ml). The organic phase is washed with brine, dried over magnesium sulphate, filtered and then evaporated to dryness under reduced pressure.

The title product is obtained in the form of a colourless oil which is used without subsequent purification.

EXAMPLE 1

({[(1Z)-2,2-Diethyl-1-oxidohydrazano]amino}oxy) methyl 3-{[({(2-chloro-5-[(2-methyl-5-nitro-2,3-dihydro-1H-indol-1-yl)carbamoyl]phenyl}-sulphonyl)amino]methyl}benzoate Step A: tert-Butyl [(2-chloro-5-{[(2-methyl-2,3-dihydro-1H-indol-1-yl)amino]carbonyl}phenyl)sulphonyl]carbamate Suspend 3-(aminosulphonyl)-4-chloro-N-(2-methyl-2,3-dihydro-1H-indol-1-yl)benzamide ($1.37 \times 10^{-2}$ mol) in dichloromethane (125 ml) and place under vigorous stirring. Add triethylamine ($1.50 \times 10^{-2}$ mol), 4-dimethylaminopyridine ($1.36 \times 10^{-3}$ mol) and then a solution of di-tert-butyl dicarbonate ($1.57 \times 10^{-2}$ mol) in dichloromethane (50 ml). Evolution of gas is observed and rapidly the reaction mixture becomes perfectly clear. After 1 hour and 30 minutes, the reaction mixture is concentrated to dryness using a rotary evaporator. The residue obtained is taken up in ethyl acetate (50 ml) and then washed with water (200 ml). The aqueous phase is acidified with 1N hydrochloric acid solution in water and then extracted with dichloromethane. The organic phase is washed with water and then with brine, dried over magnesium sulphate, filtered and evaporated to dryness under reduced pressure to yield the title product in the form of a lemon-yellow solid which is used without subsequent purification.

Step B: Methyl 3-({(tert-butoxycarbonyl)[(2-chloro-5-{[(2-methyl-2,3-dihydro-1H-indol-1-yl)amino]carbonyl}phenyl)sulphonyl]-amino}methyl)benzoate Dissolve the compound obtained in Step A ($1.29 \times 10^{-3}$ mol) in acetonitrile (6 ml), add diisopropylethylamine ($1.54 \times 10^{-3}$ mol) and place under stirring. Add methyl-3-bromomethylbenzoate ($1.41 \times 10^{-3}$ mol) and heat the reaction mixture at 80° C. After heating for 3 hours, the mixture is evaporated to dryness using a rotary evaporator. The crude product obtained is chromatographed on a silica column using as eluant a 90/10 then 75/25 n-heptane/ethyl acetate mixture.

The title product is obtained in the form of a yellow solid.

Step C: 3-({(tert-Butoxycarbonyl)[(2-chloro-5-{[(2-methyl-2,3-dihydro-1H-indol-1-yl)amino]carbonyl}phenyl)sulphonyl]amino}methyl)-benzoic Acid Dissolve the compound obtained in Step B ($1.14 \times 10^{-3}$ mol) in an acetonitrile/water (40 ml/8 ml) mixture. Add lithium hydroxide ($1.14 \times 10^{-2}$ mol) and heat at 50° C. with stirring. After heating for 2 hours, the reaction mixture is poured into water (100 ml). Extract 3 times with ethyl acetate (50 ml). The organic phase is then washed with water and then with brine, dried over magnesium sulphate, filtered and evaporated to dryness under reduced pressure.

After drying under a vacuum ramp, the title product is obtained in the form of a brown solid and is used without subsequent purification.

Step D: ({[(1Z)-2,2-Diethyl-1-oxidohydrazono]amino}oxy)methyl 3-({(tert-butoxycarbonyl)[(2-chloro-5-{[(2-methyl-5-nitro-2,3-dihydro-1H-indol-1-yl)amino]carbonyl}phenyl)sulphonyl]amino}methyl)-benzoate Dissolve the compound obtained in Step C ($8.41 \times 10^{-4}$ mol) in dimethylformamide (5 ml). Place under stirring and under nitrogen, and then add a solution of N—[(Z)-(chloromethoxy)-NNO-azoxy]-N-ethylethanamine ($9.25 \times 10^{-4}$ mol) in dimethylformamide (4 ml). Add caesium carbonate in one go ($8.41 \times 10^{-4}$ mol) and leave the reaction mixture at ambient temperature with stirring. After 2 hours, the mixture is poured into water (50 ml). Extract 3 times with ethyl acetate (20 ml). The organic phase is washed with brine, dried over magnesium sulphate, filtered and concentrated under reduced pressure. The oily orange-coloured crude product obtained is chromatographed on a silica column using as eluant a 65/35 then 50/50 n-heptane/ethyl acetate mixture.

The title product is obtained in the form of a yellow solid.

Step E: ({[(1Z)-2,2-Diethyl-1-oxidohydrazono]amino}oxy)methyl 3-{[({2-chloro-5-[(2-methyl-5-nitro-2,3-dihydro-1H-indol-1-yl)carbamoyl]phenyl}sulphonyl)amino]methyl}benzoate Dissolve the compound obtained in Step D ($4.38 \times 10^{-4}$ mol) in dioxane (25 ml). Place under stirring and then add 37% hydrochloric acid (3.5 ml) and heat at 70° C. After 2 hours, the reaction mixture is poured into water (50 ml). Extract 3 times with ethyl acetate (20 ml). The organic phase is washed with water and then with brine, dried over magnesium sulphate, filtered and concentrated using a rotary evaporator. The oily orange-coloured crude product obtained is chromatographed on a silica column using as eluant a 60/40 n-heptane/ethyl acetate mixture.

After drying under a vacuum ramp at 60° C., the title product is obtained in the form of a slightly yellow solid.

| Melting point: 85-86° C. | | | | |
|---|---|---|---|---|
| Elemental microanalysis: | C | H | N | S |
| % theoretical: | 50.47 | 4.67 | 14.21 | 4.65 |
| % experimental: | 51.14 | 5.04 | 13.19 | 4.55 |

EXAMPLE 2

({[(1Z)-2,2-Diethyl-1-oxidohydrazono]amino}oxy)methyl 3-{[({2-chloro-5-[(2-methyl-2,3-dihydro-1H-indol-1-yl)carbamoyl]phenyl}sulphonyl)-amino]methyl}benzoate Step A: ({[(1Z)-2,2-Diethyl-1-oxidohydrazono]amino}oxy)methyl 3-({(tert-butoxycarbonyl)[(2-chloro-5-{[(2-methyl-2,3-dihydro-1H-indol-1-yl)amino]carbonyl}phenyl)sulphonyl]amino}methyl)benzoate The product obtained in Step C of Example 1 is reacted with N—[(Z)-(chloromethoxy)-NNO-azoxy]-N-ethylethanamine in accordance with the process conditions described in Step D of Example 1. The title product is obtained in the form of a yellow solid after chromatography on a silica column using as eluant a 65/35 n-heptane/ethyl acetate mixture.

Step B: ({[(1Z)-2,2-Diethyl-1-oxidohydrazono]amino}oxy)methyl 3-{[({2-chloro-5-[(2-methyl-2,3-dihydro-1H-indol-1-yl)carbamoyl]phenyl}sulphonyl)amino]methyl}benzoate The procedure is identical to Step E of Example 1, starting from the compound obtained in Step A. The title product is obtained in the form of a whitish solid after chromatography on a silica column using as eluant a 60/40 n-heptane/ethyl acetate mixture. It is subsequently dried under a vacuum ramp at 60° C. for 24 hours.

| Melting point: 66-67° C. | | | | |
|---|---|---|---|---|
| Elemental microanalysis: | C | H | N | S |
| % theoretical: | 53.99 | 5.16 | 13.03 | 4.97 |
| % experimental: | 54.76 | 5.50 | 12.20 | 4.98 |

EXAMPLE 3 tert-Butyl({2-chloro-5-[(2-methyl-2,3-dihydro-1H-indol-1-yl)carbamoyl]phenyl}sulphonyl)[({[(1Z)-2,2-diethyl-1-oxidohydrazono]-amino}oxy)methyl]carbamate The product obtained in Step A of Example 4 ($1.00 \times 10^{-3}$ mol) is dissolved in acetonitrile (5 ml). The solution is placed under stirring. Add diisopropylethylamine (1.20×10⁻³ mol) and then a solution of N—[(Z)-(chloromethoxy)-NNO-azoxy]-N-ethylethanamine (1.10×10⁻³ mol) in acetonitrile (2 ml). Heat the reaction mixture at 70° C. for 2 hours and 30 minutes. Pour the reaction mixture into water (20 ml) and extract 3 times with ethyl acetate (15 ml). The organic phase is washed with water and then with brine, dried over magnesium sulphate, filtered and concentrated to dryness using a rotary evaporator. The oily orange-coloured crude product obtained is chromatographed on a silica column using as eluant an 80/20 n-heptane/ethyl acetate mixture. A yellowish solid is recovered.

The title product is obtained in the form of an orange-coloured solid after gel-filtration through Sephadex LH-20 using as eluant a 1/1 acetone/dichloromethane mixture.

| Melting point: 80-81° C. | | | | |
|---|---|---|---|---|
| Elemental microanalysis: | C | H | N | S |
| % theoretical: | 51.10 | 5.77 | 13.75 | 5.25 |
| % experimental: | 51.36 | 5.90 | 13.16 | 5.34 |

EXAMPLE 4

({[(1Z)-2,2-Diethyl-1-oxidohydrazono]amino}oxy)methyl N-(tert-butoxycarbonyl)-N-({2-chloro-5-[(2-methyl-2,3-dihydro-1H-indol-1-yl)carbamoyl]phenyl}sulphonyl)glycinate

Step A: Benzyl N-(tert-butoxycarbonyl)-N-[(2-chloro-5-{[(2-methyl-2,3-dihydro-1H-indol-1-yl)amino]carbonyl}phenyl)sulphonyl]-glycinate The compound obtained in Step A of Example 1 is reacted with benzyl bromoacetate in accordance with the process conditions described in Step B of Example 1. The oily yellowish crude product obtained is chromatographed on a silica column using as eluant an 80/20 n-heptane/ethyl acetate mixture.

The title product is obtained in the form of a slightly yellow solid.

Step B: N-(tert-Butoxycarbonyl)-N-[(2-chloro-5-{[(2-methyl-2,3-dihydro-1H-indol-1-yl)amino]carbonyl}phenyl)sulphonyl]glycine The compound obtained in Step A (1.34×10⁻³ mol) is dissolved in ethyl acetate (50 ml). Add palladium-on-carbon catalyst (10%, 82 mg) and then place the reaction mixture under hydrogen at ambient temperature and atmospheric pressure. After 24 hours, the reaction mixture is filtered through Celite and then the filtrate is evaporated to dryness under reduced pressure. The oily orange-coloured residue obtained is chromatographed on a silica column using as eluant dichloromethane and then a 98/2, 95/5 and 90/10 dichloromethane/methanol mixture.

The title product is obtained in the form of a yellowish solid.

Step C: ({[(1Z)-2,2-Diethyl-1-oxidohydrazono]amino}oxy)methyl N-(tert-butoxycarbonyl)-N-({2-chloro-5-[(2-methyl-2,3-dihydro-1H-indol-1-yl)carbamoyl]phenyl}sulphonyl)glycinate Dissolve the product obtained in Step B (1.01×10⁻³ mol) in dimethylformamide (5 ml). Place under stirring and add a solution of N—[(Z)-(chloromethoxy)-NNO-azoxy]-N-ethylethanamine (2.23×10⁻³ mol) in dimethylformamide (3 ml). Subsequently, add caesium carbonate in one go (1.01×10⁻³ mol). After 2 hours, the reaction mixture is poured into water (30 ml). Extract 3 times with ethyl acetate (20 ml). The organic phase is washed with water and then with brine, dried over magnesium sulphate, filtered and concentrated under reduced pressure. The residue obtained is chromatographed on a silica column using as eluant an 80/20 then 70/30 n-heptane/ethyl acetate mixture.

The title product is obtained in the form of a slightly yellow solid.

| Melting point: 76-77° C. | | | | |
|---|---|---|---|---|
| Elemental microanalysis: | C | H | N | S |
| % theoretical: | 50.26 | 5.57 | 12.56 | 4.79 |
| % experimental: | 50.34 | 5.74 | 12.36 | 4.65 |

EXAMPLE 5

({[(1Z)-2,2-Diethyl-1-oxidohydrazono]amino}oxy)methyl N-({2-chloro-5-[(2-methyl-2,3-dihydro-1H-indol-1-yl)carbamoyl]phenyl}sulphonyl)-glycinate The compound obtained in Step C of Example 4 (4.06×10⁻⁴ mol) is dissolved in dichloromethane (12 ml). The solution is cooled to 0° C. and placed under stirring. Add trifluoroacetic acid (4.06×10⁻³ mol). After 1 hour, the reaction mixture is placed at ambient temperature. After 3 days, the mixture is concentrated to dryness using a rotary evaporator. The oily crude product recovered is chromatographed on a silica column using as eluant a 60/40 then 50/50 n-heptane/ethyl acetate mixture.

The title product is obtained in the form of a yellow solid after gel-filtration through Sephadex LH-20 using as eluant a 1/1 acetone/dichloromethane mixture.

| Melting point: 68-69° C. | | | | |
|---|---|---|---|---|
| Elemental microanalysis: | C | H | N | S |
| % theoretical: | 48.55 | 5.14 | 14.77 | 5.64 |
| % experimental: | 48.16 | 5.24 | 14.17 | 5.46 |

EXAMPLE 6

[(tert-Butoxycarbonyl)({2-chloro-5-[(2-methyl-2,3-dihydro-1H-indol-1-yl)carbamoyl]phenyl}sulphonyl)amino]methyl({[(1Z)-2,2-diethyl-1-oxidohydrazono]amino}oxy)methyl pentanedioate

Step A: Benzyl [(tert-butoxycarbonyl)({2-chloro-5-[(2-methyl-2,3-dihydro-1H-indol-1-yl)carbamoyl]phenyl}sulphonyl)amino]methyl pentanedioate Dissolve the compound obtained in Step A of Example 1 (2.15×10⁻³ mol) in acetonitrile (10 ml) and place the solution under stirring. Add diisopropylethylamine (2.57×10⁻³ mol) and then a solution of intermediate 3 (2.36×10⁻³ mol) in acetonitrile (10 ml). During the addition, the reaction mixture turns reddish and then rapidly becomes colourless. Heat the mixture at 60° C. After 1 hour and 30 minutes, the reaction mixture is evaporated to dryness under reduced pressure. The solid yellow residue obtained is chromatographed on a silica column using as eluant an 80/20 then 70/30 n-heptane/ethyl acetate mixture.

The title product is obtained in the form of a yellow solid.

Step B: 5-{[(tert-Butoxycarbonyl)({2-chloro-5-[(2-methyl-2,3-dihydro-1H-indol-1-yl)carbamoyl]phenyl}sulphonyl)amino]methoxy}-5-oxopentanoic Acid Dissolve the compound obtained in Step A (1.45×10$^{-3}$ mol) in ethyl acetate (100 ml). Add palladium-on-carbon catalyst (10%, 100 mg) and then at ambient temperature place the reaction mixture under hydrogen at atmospheric pressure. After 36 hours, the reaction mixture is filtered through Celite and new palladium-on-carbon catalyst is again added (10%, 100 mg). The mixture is placed under hydrogen again, under the same conditions as those described hereinabove, for an additional 24 hours. The reaction is then terminated, the mixture is filtered through Celite and then the filtrate is evaporated to dryness under reduced pressure. The residue obtained is chromatographed on a silica column using as eluant a 98/2 then 97/3 dichloromethane/methanol mixture.

The title product is obtained in the form of a cream-coloured solid.

Step C: [(tert-Butoxycarbonyl)({2-chloro-5-[(2-methyl-2,3-dihydro-1H-indol-1-yl)carbamoyl]phenyl}sulphonyl)amino]methyl({[(1Z)-2,2-diethyl-1-oxidohydrazono]amino}oxy)methyl pentanedioate Dissolve the compound obtained in Step B (9.23×10$^{-4}$ mol) in dimethylformamide (10 ml). Place under stirring and under nitrogen, and add a solution of N—[(Z)-(chloromethoxy)-NNO-azoxy]-N-ethylethanamine (1.11×10$^{-3}$ mol) in dimethylformamide (3 ml). Subsequently, add caesium carbonate in one go (9.23×10$^{-4}$ mol). After 1 hour and 30 minutes, the reaction mixture is poured into water (100 ml). Extract 3 times with ethyl acetate (75 ml). The organic phase is washed with water and then with brine. It is subsequently dried over magnesium sulphate, filtered and then evaporated to dryness under reduced pressure. The oily orange-coloured residue obtained is purified by chromatography on a silica column using as eluant a 70/30 then 60/40 n-heptane/ethyl acetate mixture. A second, reverse-phase, chromatography on a Lichroprep RP-18 column is necessary. The elution conditions are as follows: (eluant A: 1000 ml H$_2$O/25 ml CH$_3$CN; eluant B: 25 ml H$_2$O/1000 ml CH$_3$CN) 10% of B for 15 minutes, from 10 to 75% of B in 60 minutes, from 75 to 100% of B in 20 minutes.

The title product is obtained in the form of a slightly yellowish meringue.

| Elemental microanalysis: | C | H | N | S |
|---|---|---|---|---|
| % theoretical: | 50.89 | 5.74 | 11.13 | 4.25 |
| % experimental: | 50.83 | 5.74 | 11.16 | 3.99 |

EXAMPLE 7

[(tert-Butoxycarbonyl)({2-chloro-5-[(2-methyl-2,3-dihydro-1H-indol-1-yl)carbamoyl]phenyl}sulphonyl)amino]methyl ({[(1Z)-2,2-diethyl-1-oxidohydrazono]amino}oxy)methyl butanedioate Step A: Benzyl [(tert-butoxycarbonyl)({2-chloro-5-[(2-methyl-2,3-dihydro-1H-indol-1-yl)carbamoyl]phenyl}sulphonyl)amino]methyl butanedioate Dissolve the compound obtained in Step A of Example 1 (1.50×10$^{-3}$ mol) in acetonitrile (7 ml) and place the solution under stirring. Add diisopropylethylamine (1.80×10$^{-3}$ mol) and then a solution of intermediate 6 (1.65×10$^{-3}$ mol) in acetonitrile (7 ml). During the addition, the reaction mixture turns reddish and then rapidly becomes colourless. Heat the mixture at 55° C. After about 30 minutes, the reaction mixture is evaporated to dryness under reduced pressure. The solid lemon-yellow residue obtained is chromatographed on a silica column using as eluant an 80/20, 70/30 then 60/40 n-heptane/ethyl acetate mixture.

The title product is obtained in the form of a yellow meringue.

Step B: 4-{[(tert-Butoxycarbonyl)({2-chloro-5-[(2-methyl-2,3-dihydro-1H-indol-1-yl)carbamoyl]phenyl}sulphonyl)amino]methoxy}-4-oxobutanoic Acid Dissolve the compound obtained in Step A (1.08×10$^{-3}$ mol) in ethyl acetate (75 ml). Add palladium-on-carbon catalyst (10%, 75 mg) and then at ambient temperature place the reaction mixture under hydrogen at atmospheric pressure. After 36 hours, the reaction mixture is filtered through Celite and new palladium-on-carbon catalyst is again added (10%, 75 mg). The mixture is placed under hydrogen again under the same conditions as those described hereinabove for an additional 24 hours. The reaction is then terminated, the mixture is filtered through Celite and then the filtrate is evaporated to dryness under reduced pressure. The residue obtained is chromatographed on a silica column using as eluant a 98/2 dichloromethane/methanol mixture.

The title product is obtained in the form of a cream-coloured solid.

Step C: [(tert-Butoxycarbonyl)({2-chloro-5-[(2-methyl-2,3-dihydro-1H-indol-1-yl)carbamoyl]phenyl}sulphonyl)amino]methyl({[(1Z)-2,2-diethyl-1-oxidohydrazono]amino}oxy)methyl butanedioate Dissolve the compound obtained in Step B (8.30×10$^{-4}$ mol) in dimethylformamide (9 ml). Place under stirring and under nitrogen, and add a solution of N—[(Z)-(chloromethoxy)-NNO-azoxy]-N-ethylethanamine (9.96×10$^{-4}$ mol) in dimethylformamide (3 ml). Subsequently, add caesium carbonate in one go (8.30×10$^{-4}$ mol). After 1 hour, the reaction mixture is poured into water (100 ml). Extract 3 times with ethyl acetate (75 ml). The organic phase is washed with water and then with brine. It is subsequently dried over magnesium sulphate, filtered and then evaporated to dryness under reduced pressure. The oily orange-coloured residue obtained is purified by chromatography on a silica column using as eluant a 70/30 then 60/40 n-heptane/ethyl acetate mixture. A second, reverse-phase, chromatography on a Lichroprep RP-18 column (60×400 mm) is necessary. The elution conditions are as follows: (eluant A: 1000 ml $H_2O$/25 ml $CH_3CN$; eluant B: 25 ml $H_2O$/1000 ml $CH_3CN$) A/B: 40/60; flow rate: 12 ml/min.

The title product is obtained in the form of an orange-coloured meringue.

| Elemental microanalysis: | C | H | N | S |
|---|---|---|---|---|
| % theoretical: | 50.23 | 5.58 | 11.34 | 4.33 |
| % experimental: | 50.51 | 5.67 | 10.91 | 4.48 |

EXAMPLE 8

({[(1Z)-2,2-diethyl-1-oxidohydrazono]amino}oxy)methyl 4-{[({2-chloro-5-[(2-methyl-2,3-dihydro-1H-indol-1-yl)carbamoyl]phenyl}sulphonyl)-amino]-methyl}benzoate Step A: Methyl 4-{[(tert-butoxycarbonyl)({2-chloro-5-[(2-methyl-2,3-dihydro-1H-indol-1-yl)carbamoyl]phenyl}sulphonyl)amino]-methyl}benzoate Dissolve the compound obtained in Step A of Example 1 ($1.72 \times 10^{-3}$ mol) in acetonitrile (8 ml) and place the solution under stirring. Add diisopropylethylamine ($2.06 \times 10^{-3}$ mol) and then, after stirring for 10 minutes, methyl 4-bromomethylbenzoate ($2.57 \times 10^{-3}$ mol). Heat the mixture at 60° C. After 2 hours and 30 minutes, the reaction mixture is poured into water (30 ml). Extract 3 times with ethyl acetate (20 ml). The organic phase is washed with brine, dried over magnesium sulphate, filtered and evaporated to dryness under reduced pressure. The oily orange-coloured residue obtained is chromatographed on a silica column using as eluant a 90/10 to 75/25 n-heptane/ethyl acetate mixture.

The title product is obtained in the form of a yellow meringue.

Step B: 4-{[(tert-Butoxycarbonyl)({2-chloro-5-[(2-methyl-2,3-dihydro-1H-indol-1-yl)carbamoyl]phenyl}sulphonyl)amino]methyl}benzoic Acid Dissolve the compound obtained in Step A ($1.30 \times 10^{-3}$ mol) in a mixture of acetonitrile (45 ml) and water (9 ml). Add lithium hydroxide ($1.30 \times 10^{-2}$ mol) and heat at 50° C. with stirring. After heating for 5 hours, the dark-brown reaction mixture is poured into water (100 ml). Extract 3 times with ethyl acetate (50 ml). The organic phase is then washed with water and then with brine, dried over magnesium sulphate, filtered and evaporated to dryness under reduced pressure.

After drying under a vacuum ramp, the title product is obtained in the form of a brown meringue which is used without subsequent purification.

Step C: ({[(1Z)-2,2-Diethyl-1-oxidohydrazono]amino}oxy)methyl 4-{[(tert-butoxycarbonyl)({2-chloro-5-[(2-methyl-2,3-dihydro-1H-indol-1-yl)carbamoyl]phenyl}sulphonyl)amino]methyl}benzoate Dissolve the compound obtained in Step B ($8.96 \times 10^{-4}$ mol) in dimethylformamide (8 ml). Place under stirring and under nitrogen, and then add a solution of N—[(Z)-(chloromethoxy)-NNO-azoxy]-N-ethylethanamine ($1.17 \times 10^{-3}$ mol) in dimethylformamide (1 ml). Add caesium carbonate in one go ($9.41 \times 10^{-4}$ mol) and leave the reaction mixture at ambient temperature with stirring. After 2 hours, the mixture is poured into water (50 ml). Extract 3 times with ethyl acetate (20 ml). The organic phase is washed with brine, dried over magnesium sulphate, filtered and concentrated under reduced pressure.

The oily orange-coloured crude product obtained is chromatographed on a silica column using as eluant a 65/35 n-heptane/ethyl acetate mixture.

The title product is obtained in the form of a yellow solid.

Step D: ({[1Z)-2,2-Diethyl-1-oxidohydrazono]amino}oxy)methyl 4-{[({2-chloro-5-[(2-methyl-2,3-dihydro-1H-indol-1-yl(carbamoyl]-phenyl}sulphonyl)amino]methyl}benzoate Dissolve the compound obtained in Step C ($4.74 \times 10^{-4}$ mol) in 1,4-dioxane (5 ml). Place the solution under stirring at ambient temperature and then add 10 ml of a 4N solution of HCl in 1,4-dioxane. The initially yellowish reaction mixture becomes darker and darker until it is virtually black. After stirring for 2 days at ambient temperature, the reaction mixture is evaporated to dryness under reduced pressure. The black residue obtained is chromatographed on a silica column using as eluant a 50/50 n-heptane/ethyl acetate mixture.

After recrystallisation from n-heptane; the title product is obtained in the form of a white solid.

| Melting point: 96-97° C. | | | | |
|---|---|---|---|---|
| Elemental microanalysis: | C | H | N | S |
| % theoretical: | 53.99 | 5.16 | 13.03 | 4.97 |
| % experimental: | 54.24 | 5.27 | 12.65 | 4.60 |

EXAMPLE 9

({[(1Z)-2,2-Diethyl-1-oxidohydrazono]amino}oxy)methyl2-{[(tert-butoxycarbonyl)({2-chloro-5-[(2-methyl-2,3-dihydro-1H-indol-1-yl)carbamoyl]phenyl}sulphonyl)amino]methyl}benzoate Step A: Methyl 2-{[(tert-butoxycarbonyl)({2-chloro-5-[(2-methyl-2,3-dihydro-1H-indol-1-yl)carbamoyl]phenyl}sulphonyl)amino]-methyl}benzoate Dissolve the compound obtained in Step A of Example 1 ($1.72 \times 10^{+3}$ mol) in acetonitrile (8 ml) and place the solution under stirring. Add diisopropylethylamine ($2.06 \times 10^{-3}$ mol) and then, after stirring for 10 minutes, intermediate 7 ($2.62 \times 10^{-3}$ mol). Heat the mixture at 60° C. After 5 hours, the reaction mixture is poured into water (30 ml). Extract 3 times with ethyl acetate (20 ml). The organic phase is washed with brine, dried over magnesium sulphate, filtered and evaporated to dryness under reduced pressure. The oily orange-brown residue obtained is chromatographed on a silica column using as eluant a 90/10 to 65/35 n-heptane/ethyl acetate mixture.

The title product is obtained in the form of a yellow meringue.

Step B: 2-{[(tert-Butoxycarbonyl)({2-chloro-5-[(2-methyl-2,3-dihydro-1H-indol-1-yl)carbamoyl]phenyl}sulphonyl)amino]methyl}benzoic Acid Dissolve the compound obtained in Step A ($1.26 \times 10^{-3}$ mol) in a mixture of acetonitrile (45 ml) and water (9 ml). Add lithium hydroxide (1.26×10⁻² mol) and heat at 50° C. with stirring. After heating for 5 hours and 30 minutes, the dark-brown reaction mixture is poured into water (100 ml). Extract 3 times with ethyl acetate (50 ml). The organic phase is then washed with water and then with brine, dried over magnesium sulphate, filtered and evaporated to dryness under reduced pressure.

After drying under a vacuum ramp, the title product is obtained in the form of a brown meringue which is used without subsequent purification.

Step C: ({[(1Z)-2,2-Diethyl-1-oxidohydrazono]amino}oxy)methyl 2-{[(tert-butoxycarbonyl)({2-chloro-5-[(2-methyl-2,3-dihydro-1H-indol-1-yl)carbamoyl]phenyl}sulphonyl)amino]methyl}benzoate Dissolve the compound obtained in Step B (8.25×10⁻⁴ mol) in dimethylformamide (8 ml). Place under stirring and under nitrogen, and then add a solution of N—[(Z)-(chloromethoxy)-NNO-azoxy]-N-ethylethanamine (1.07×10⁻³ mol) in dimethylformamide (2 ml). Add caesium carbonate in one go (8.66×10⁻⁴ mol) and leave the reaction mixture at ambient temperature with stirring. After 3 hours, the mixture is poured into water (50 ml). Extract 3 times with ethyl acetate (20 ml). The organic phase is washed with brine, dried over magnesium sulphate, filtered and concentrated under reduced pressure.

The oily brown crude product obtained is chromatographed on a silica column using as eluant a 70/30 n-heptane/ethyl acetate mixture. A second, reverse-phase, chromatography on a Lichroprep RP-18 column is necessary. The elution conditions are as follows: (eluant A: 1000 ml H₂O/25 ml CH₃CN; eluant B: 25 ml H₂O/1000 ml CH₃CN) 20% of B for 15 minutes, from 20 to 83% of B in 60 minutes, from 83 to 100% of B in 15 minutes.

After recrystallisation from an n-heptane/ethyl acetate mixture, the title product is obtained in the form of a yellow solid.

| Melting point: 79-81° C. | | | | |
|---|---|---|---|---|
| Elemental microanalysis: | C | H | N | S |
| % theoretical: | 54.80 | 5.54 | 11.28 | 4.30 |
| % experimental: | 54.57 | 5.65 | 10.82 | 3.88 |

EXAMPLE 10

({[(1Z)-2,2-diethyl-1-oxidohydrazono]amino}oxy)methyl 4-({[(2-chloro-5-{[(2R)-2-methyl-2,3-dihydro-1H-indol-1-yl]carbamoyl}phenyl)-sulphonyl]amino}methyl)benzoate Step A: tert-Butyl [(2-chloro-5-{[(2R)-2-methyl-2,3-dihydro-1H-indol-1-yl]carbamoyl}phenyl)sulphonyl]carbamate Suspend intermediate 8 (6.0×10⁻³ mol) in dichloromethane (55 ml) and place under vigorous stirring. Add triethylamine (6.60×10⁻³ mol), 4-dimethylaminopyridine (6.0×10⁻⁴ mol) and then a solution of di-tert-butyl dicarbonate (6.90×10⁻³ mol) in dichloromethane (20 ml). Evolution of gas is observed and the reaction mixture rapidly becomes perfectly clear. After 1 hour and 30 minutes, the reaction mixture is poured into water (100 ml). Extract 3 times with dichloromethane (50 ml). The organic phase is then washed with water and then with brine, dried over magnesium sulphate, filtered and evaporated to dryness under reduced pressure.

The title product is obtained in the form of a lemon-yellow solid which is used without subsequent purification.

Step B: Methyl 4-({(tert-butoxycarbonyl)[(2-chloro-5-{[(2R)-2-methyl-2,3-dihydro-1H-indol-1-yl]carbamoyl}phenyl)sulphonyl]amino}-methyl)benzoate Dissolve the compound obtained in Step A (7.57×10⁻³ mol) in acetonitrile (35 ml) and place the solution under stirring. Add diisopropylethylamine (9.09×10⁻³ mol) and then, after stirring for 10 minutes, methyl 4-bromomethyl-benzoate (1.15×10⁻⁴ mol). Heat the mixture at 60° C. After one night, the reaction mixture is poured into water (100 ml). Extract 3 times with ethyl acetate (50 ml). The organic phase is washed with brine, dried over magnesium sulphate, filtered and evaporated to dryness under reduced pressure. The residue obtained is triturated in an n-heptane/ethyl acetate mixture, bringing about the precipitation of a solid which is recovered by filtration.

The title product is obtained in the form of a white solid.

Step C: 4-({(tert-Butoxycarbonyl)[(2-chloro-5-{[(2R)-2-methyl-2,3-dihydro-1H-indol-1-yl]carbamoyl}phenyl)sulphonyl]amino}-methyl)benzoic Acid Dissolve the compound obtained in Step B (5.03×10⁻³ mol) in a mixture of acetonitrile (175 ml) and water (35 ml). Add lithium hydroxide (5.03×10⁻² mol) and heat at 50° C. with stirring. After heating for 3 hours, the dark-brown reaction mixture is poured into water (200 ml). Extract 3 times with ethyl acetate (150 ml). The organic phase is then washed with water and then with brine, dried over magnesium sulphate, filtered and evaporated to dryness under reduced pressure. The oily residue obtained is triturated in an n-heptane/ethyl acetate mixture, bringing about precipitation of a solid which is recovered by filtration.

The title product is obtained in the form of a cream-coloured solid.

Step D: ({[(1Z)-2,2-Diethyl-1-oxidohydrazono]amino}oxy)methyl 4-({(tert-butoxycarbonyl)[(2-chloro-5-{[(2R)-2-methyl-2,3-dihydro-1H-indol-1-yl]carbamoyl}phenyl)sulphonyl]amino}methyl)benzoate Dissolve the compound obtained in Step C (2.90×10⁻³ mol) in dimethylformamide (30 ml). Place under stirring and under nitrogen, and then add a solution of N—[(Z)-(chloromethoxy)-NNO-azoxy]-N-ethylethanamine (4.88×10⁻³ mol) in dimethylformamide (3 ml). Add caesium carbonate in one go (3.05×10⁻³ mol) and leave the reaction mixture at ambient temperature with stirring. After 3 hours and 30 minutes, the mixture is poured into water (200 ml). Extract 3 times with ethyl acetate (150 ml). The organic phase is washed with brine, dried over magnesium sulphate, filtered and concentrated under reduced pressure.

The oily orange-coloured crude product obtained is chromatographed on a silica column using as eluant a 65/35 n-heptane/ethyl acetate mixture.

The title product is obtained in the form of a yellow solid.

Step E: ({[(1Z)-2,2-Diethyl-1-oxidohydrazono]amino}oxy)methyl 4-({[(2-chloro-5-{[(2R)-2-methyl-2,3-dihydro-1H-indol-1-yl]carbamoyl}-phenyl)sulphonyl]amino}methyl)benzoate Dissolve the compound obtained in Step D (1.47×10⁻³ mol) in 20 ml of a 4N solution of HCl in 1,4-dioxane and place under stirring. The initially yellowish reaction mixture becomes darker and darker until it is virtually black. After stirring for 18 hours at ambient temperature, the reaction mixture is evaporated to dryness under reduced pressure. The black residue obtained is chromatographed on a silica column using as eluant a 50/50 n-heptane/ethyl acetate mixture.

After recrystallisation from n-heptane, the title product is obtained in the form of a white solid.

| Melting point: 78-79° C. | | | | |
|---|---|---|---|---|
| Elemental microanalysis: | C | H | N | S |
| % theoretical: | 53.99 | 5.16 | 13.03 | 4.97 |
| % experimental: | 53.77 | 4.94 | 12.90 | 5.06 |

EXAMPLE 11

({[(1Z)-2,2-diethyl-1-oxidohydrazono]amino}oxy)methyl hydrogen ({2-chloro-5-[(2-methyl-2,3-dihydro-1H-indol-1-yl)carbamoyl]phenyl}sulphonyl)amidophosphate Step A: Diethyl({2-chloro-5-[(2-methyl-2,3-dihydro-1H-indol-1-yl)-carbamoyl]phenyl}sulphonyl)amidophosphate In a three-necked flask fitted with two addition ampoules, dissolve 3-(aminosulphonyl)-4-chloro-N-(2-methyl-2,3-dihydro-1H-indol-1-yl)benzamide ($1.37 \times 10^{-2}$ mol) in aqueous 1N sodium hydroxide solution (25 ml). The lemon-yellow solution obtained is placed under stirring at ambient temperature and under nitrogen. Add dropwise a solution of diethyl chlorophosphate ($9.56 \times 10^{-2}$ mol) in tetrahydrofuran (50 ml) and simultaneously aqueous 3N sodium hydroxide solution (45 ml) in such a manner as to keep the reaction mixture perfectly homogeneous. When the addition is complete, the reaction mixture is left at ambient temperature for 2 hours. Pour the reaction mixture into water (200 ml) and extract 3 times with ethyl acetate. The aqueous phase is acidified to pH 4 and then extracted again with ethyl acetate. The organic phases are combined, dried over magnesium sulphate, filtered and evaporated to dryness under reduced pressure.

The title product is obtained in the form of an orange-coloured oil which is used without subsequent purification.

Step B: ({2-Chloro-5-[(2-methyl-2,3-dihydro-1H-indol-1-yl)carbamoyl]-phenyl}sulphonyl)phosphoramidic Acid Dissolve the compound obtained in Step A ($1.22 \times 10^{-2}$ mol) in dichloromethane (130 ml). Place the solution under stirring at 0° C. and under nitrogen. Subsequently, add dropwise trimethylsilyl iodide ($5.41 \times 10^{-2}$ mol). When the addition is complete, leave to return to ambient temperature, with stirring. After 18 hours, the reaction mixture is evaporated to dryness under reduced pressure. Take up the brown residue in a 25 ml/1 ml acetone/water mixture, stir for 15 minutes and then evaporate to dryness again. The brown residue obtained in the form of a meringue is purified by reverse-phase chromatography on a Lichroprep RP-18 column. The elution conditions are as follows: (eluant A: 1000 ml $H_2O$/25 ml $CH_3CN$; eluant B: 25 ml $H_2O$/1000 ml $CH_3CN$) 100% of A; 95/5 then 90/10 A/B.

The fractions containing the expected product are lyophilised.

The title product is obtained in the form of a flaky yellow solid.

Step C: ({[(1Z)-2,2-diethyl-1-oxidohydrazono]amino}oxy)methyl hydrogen ({2-chloro-5-[(2-methyl-2,3-dihydro-1H-indol-1-yl)carbamoyl]phenyl}sulphonyl)amidophosphate Dissolve the compound obtained in Step B ($3.81 \times 10^{-3}$ mol) in N,N'-dimethyl-N,N'-propylurea (25 ml). Add triethylamine ($8.88 \times 10^{-3}$ mol) and then stir at ambient temperature for 10 minutes. Subsequently, add N—[(Z)-(chloromethoxy)-NNO-azoxy]-N-ethylethanamine ($15.25 \times 10^{-3}$ mol), sodium iodide ($7.62 \times 10^{-3}$ mol), and heat the reaction mixture at 50° C. After one night, the reaction mixture is poured into diethyl ether (200 ml). Filter off insoluble material, which is taken up in acetonitrile. The solid that remains in suspension is filtered off and removed and the filtrate is evaporated to dryness under reduced pressure.

The residue obtained is purified by 3 successive reverse-phase chromatographies on a Lichroprep RP-18 column. The elution conditions are as follows: (eluant A: 1000 ml $H_2O$/25 ml $CH_3CN$; eluant B: 25 ml $H_2O$/1000 ml $CH_3CN$) 5% of B for 10 minutes, from 5 to 75% of B in 60 minutes, from 75 to 100% of B in 10 minutes. The fractions containing the expected product are lyophilised.

The title product is obtained in the form of a flaky yellow solid.

| Elemental microanalysis: | C | H | N | S | Cl |
|---|---|---|---|---|---|
| % theoretical: | 42.68 | 4.78 | 14.22 | 5.43 | 6.00 |
| % experimental: | 42.58 | 5.24 | 13.20 | 5.13 | 5.62 |

EXAMPLE 12

(({[(1Z)-2,2-Diethyl-1-oxidohydrazono]amino}oxy)methyl 4-{[({2-chloro-5-[(2-methyl-2,3-dihydro-1H-indol-1-yl)carbamoyl]phenyl}sulphonyl)amino]methyl}phenyl)acetate Step A: (4-{[(tert-Butoxycarbonyl)({2-chloro-5-[(2-methyl-2,3-dihydro-1H-indol-1-yl)carbamoyl]phenyl}sulphonyl)amino]methyl}phenyl)acetic Acid Dissolve the compound obtained in Step A of Example 1 ($3.22 \times 10^{-3}$ mol) in acetonitrile (15 ml) and place the solution under stirring. Add diisopropylethylamine ($3.86 \times 10^{-3}$ mol) and then 4-bromomethylphenylacetic acid ($7.08 \times 10^{-3}$ mol). Heat the mixture at 65° C. After 3 hours, the reaction mixture is evaporated to dryness under reduced pressure. The oily orange-coloured residue obtained is chromatographed on a silica column using as eluant a 60/40 then 50/50 n-heptane/ethyl acetate mixture.

The title product is obtained in the form of a whitish solid.

Step B: ({[(1Z)-2,2-Diethyl-1-oxidohydrazono]amino}oxy)methyl (4-{[(tert-butoxycarbonyl)({2-chloro-5-[(2-methyl-2,3-dihydro-1H-indol-1-yl)carbamoyl]phenyl}sulphonyl)amino]methyl}phenyl)acetate Dissolve the compound obtained in Step A ($2.03 \times 10^{-3}$ mol) in dimethylformamide (10 ml). Place under stirring and under nitrogen, and then add a solution of N—[(Z)-(chloromethoxy)-NNO-azoxy]-N-ethylethanamine ($2.64 \times 10^{-3}$ mol) in dimethylformamide (2 ml). Add caesium carbonate in one go ($2.13 \times 10^{-3}$ mol) and leave the reaction mixture at ambient temperature with stirring. After 2 hours, the mixture is poured into water (60 ml). Extract 3 times with ethyl acetate (30 ml). The organic phase is washed with brine, dried over magnesium sulphate, filtered and concentrated under reduced pressure.

The oily orange-coloured crude product obtained is chromatographed on a silica column using as eluant a 65/35 n-heptane/ethyl acetate mixture.

The title product is obtained in the form of a yellow meringue.

Step C: ({[(1Z)-2,2-Diethyl-1-oxidohydrazono]
amino}oxy)methyl (4-{[({2-chloro-5-[(2-methyl-2,
3-dihydro-1H-indol-1-yl)carbamoyl]
phenyl}sulphonyl)amino]methyl}phenyl)acetate Dissolve the compound obtained in Step B ($8.86 \times 10^{-4}$ mol) in 1,4-dioxane (5 ml). Place the solution under stirring at ambient temperature and then add 10 ml of a 4N solution of HCl in 1,4-dioxane. The initially yellowish reaction mixture becomes darker and darker until it is virtually black. After stirring for 36 hours at ambient temperature, the reaction mixture is evaporated to dryness under reduced pressure. The black residue obtained is chromatographed on a silica column using as eluant a 60/40 n-heptane/ethyl acetate mixture.

The title product is obtained in the form of a slightly yellow meringue.

| Elemental microanalysis: | C | H | N | S |
|---|---|---|---|---|
| % theoretical: | 54.66 | 5.35 | 12.75 | 4.86 |
| % experimental: | 54.60 | 5.43 | 12.30 | 4.96 |

EXAMPLE 13

({[(1Z)-2,2-Diethyl-1-oxidohydrazono]amino}oxy)
methyl 4-{2-[({2-chloro-5-[(2-methyl-2,3-dihydro-
1H-indol-1-yl)carbamoyl]phenyl}sulphonyl)amino]
ethyl}benzoate Step A: Methyl 4-{2-[(tert-butoxycarbonyl)({2-
chloro-5-[(2-methyl-2,3-dihydro-1H-indol-1-yl)car-
bamoyl]phenyl}sulphonyl)amino]ethyl}-benzoate Dissolve the compound obtained in Step A of Example 1 ($1.04 \times 10^{-2}$ mol) in acetonitrile (20 ml) and place the solution under stirring. Add diisopropylethylamine ($1.24 \times 10^{-2}$ mol) and then, after stirring for 10 minutes, intermediate 9 ($2.20 \times 10^{-2}$ mol) dissolved in acetonitrile (20 ml). Heat the mixture at 60° C. After 5 days, the reaction mixture is evaporated to dryness under reduced pressure. The residue obtained is chromatographed on a silica column using as eluant a 75/25 n-heptane/ethyl acetate mixture.

The title product is obtained in the form of a pale yellow meringue.

Step B: 4-{2-[(tert-Butoxycarbonyl)({2-chloro-5-[(2-
methyl-2,3-dihydro-1H-indol-1-yl)carbamoyl]
phenyl}sulphonyl)amino]ethyl}benzoic Acid Dissolve the compound obtained in Step A ($5.10 \times 10^{-4}$ mol) in a mixture of acetonitrile (18 ml) and water (3 ml). Add lithium hydroxide ($5.10 \times 10^{-3}$ mol) and heat at 55° C. with stirring. After heating for 4 hours, the dark-brown reaction mixture is poured into water (100 ml). Extract 3 times with ethyl acetate (75 ml). The organic phase is then washed with water and then with brine, dried over magnesium sulphate, filtered and evaporated to dryness under reduced pressure.

The title product is obtained in the form of a brown meringue which is used without subsequent purification.

Step C: ({[(1Z)-2,2-Diethyl-1-oxidohydrazono]
amino}oxy)methyl 4-{2-[(tert-butoxycarbonyl)({2-
chloro-5-[(2-methyl-2,3-dihydro-1H-indol-1-yl)car-
bamoyl]phenyl}sulphonyl)amino]ethyl}benzoate Dissolve the compound obtained in Step B ($4.0 \times 10^{-4}$ mol) in dimethylformamide (3 ml). Place under stirring and under nitrogen, and add a solution of N—[(Z)'-(chloromethoxy)-NNO-azoxy]-N-ethylethanamine ($5.21 \times 10^{-4}$ mol) in dimethylformamide (2 ml). Subsequently, add caesium carbonate in one go ($4.20 \times 10^{-4}$ mol). After 1 hour, the reaction mixture is poured into water (50 ml). Extract 3 times with ethyl acetate (50 ml). The organic phase is washed with water and then with brine. It is subsequently dried over magnesium sulphate, filtered and then evaporated to dryness under reduced pressure. The oily brown residue obtained is purified by chromatography on a silica column using as eluant a 65/35 n-heptane/ethyl acetate mixture.

The title product is obtained in the form of an orange-brown meringue.

Step D: ({[(1Z)-2,2-Diethyl-1-oxidohydrazono]
amino}oxy)methyl 4-{2-[({2-chloro-5-[(2-methyl-2,
3-dihydro-1H-indol-1-yl)carbamoyl]-
phenyl}sulphonyl)amino]ethyl}benzoate Dissolve the compound obtained in Step C ($2.17 \times 10^{-4}$ mol) in 1,4-dioxane (2 ml). Place the solution under stirring at ambient temperature and then add 4 ml of a 4N solution of HCl in 1,4-dioxane. The initially yellowish reaction mixture becomes darker and darker until it is virtually black. After stirring for 40 hours at ambient temperature, the reaction mixture is evaporated to dryness under reduced pressure. The black residue obtained is chromatographed on a silica column using as eluant a 55/45 n-heptane/ethyl acetate mixture. A second, reverse-phase, chromatography on a Lichroprep RP-18 column is necessary. The elution conditions are as follows: (eluant A: 1000 ml $H_2O$/25 ml $CH_3CN$; eluant B: 25 ml $H_2O$/1000 ml $CH_3CN$) 10% of B for 20 minutes, from 10 to 80% of B in 70 minutes, from 80 to 100% of B in 15 minutes.

The title product is obtained in the form of a slightly yellow meringue.

| Elemental microanalysis: | C | H | N | S |
|---|---|---|---|---|
| % theoretical: | 54.66 | 5.35 | 12.75 | 4.86 |
| % experimental: | 54.34 | 5.43 | 12.46 | 4.72 |

EXAMPLE 14

({[(1Z)-2,2-Diethyl-1-oxidohydrazono]amino}oxy)
methyl 4-{2-[({2-chloro-5-[((2R)-2-methyl-2,3-dihydro-1H-indol-1-yl)carbamoyl]-phenyl}sulphonyl)
amino]ethyl}benzoate Starting from intermediate 8, the title product is obtained in accordance with the procedure described in Steps A to D of Example 13.

EXAMPLE 15

({[(1Z)-2,2-Diethyl-1-oxidohydrazono]amino}oxy)
methyl 4-{1-[({2-chloro-5-[(2-methyl-2,3-dihydro-1H-indol-1yl)carbamoyl]phenyl}-sulphonyl)amino]
ethyl}benzoate Step A: Methyl 4-{1-[(tert-butoxycarbonyl)({2-chloro-5-[(2-methyl-2,3-dihydro-1H-indol-1-yl)carbamoyl]phenyl}sulphonyl)amino]ethyl}-benzoate Dissolve the compound obtained in Step A of Example 1 ($2.42 \times 10^{-3}$ mol) in acetonitrile (8 ml) and place the solution under stirring. Add diisopropylethylamine ($2.90 \times 10^{-3}$ mol) and then, after stirring for 10 minutes, intermediate 10 ($3.38 \therefore 10^{-3}$ mol) dissolved in acetonitrile (2 ml). Heat the mixture at 60° C. After 3 days, the reaction mixture is evaporated to dryness under reduced pressure. The oily yellow residue obtained is chromatographed on a silica column using as eluant a 75/25 n-heptane/ethyl acetate mixture.

The title product is obtained in the form of a pale yellow meringue.

Step B: 4-{1-[(tert-Butoxycarbonyl)({2-chloro-5-[(2-methyl-2,3-dihydro-1H-indol-1-yl)carbamoyl]
phenyl}sulphonyl)amino]ethyl}benzoic Acid Dissolve the compound obtained in Step A ($1.58 \times 10^{-3}$ mol) in a mixture of acetonitrile (60 ml) and water (10 ml). Add lithium hydroxide ($1.58 \times 10^{-2}$ mol) and heat at 55° C. with stirring. After heating for 4 hours, the dark-brown reaction mixture is poured into water (200 ml). Extract 3 times with ethyl acetate (100 ml). The organic phase is then washed with water and then with brine, dried over magnesium sulphate, filtered and evaporated to dryness under reduced pressure.

The title product is obtained in the form of a brown meringue which is used without subsequent purification.

Step C: ({[(1Z)-2,2-Diethyl-1-oxidohydrazono]
amino}oxy)methyl 4-{1-[(tert-butoxycarbonyl)({2-chloro-5-[(2-methyl-2,3-dihydro-1H-indol-1-yl)carbamoyl]phenyl}sulphonyl)amino]ethyl}benzoate Dissolve the compound obtained in Step B ($1.07 \times 10^{-3}$ mol) in dimethylformamide (6 ml). Place under stirring and under nitrogen, and add a solution of N—[(Z)-(chloromethoxy)-NNO-azoxy]-N-ethylethanamine ($1.40 \times 10^{-3}$ mol) in dimethylformamide (2 ml). Subsequently, add caesium carbonate in one go ($1.13 \times 10^{-3}$ mol). After 1 hour and 30 minutes, the reaction mixture is poured into water (50 ml). Extract 3 times with ethyl acetate (50 ml). The organic phase is washed with water and then with brine. It is subsequently dried over magnesium sulphate, filtered and then evaporated to dryness under reduced pressure. The oily brown residue obtained is purified by chromatography on a silica column using as eluant a 65/35 n-heptane/ethyl acetate mixture.

The title product is obtained in the form of an orange-coloured meringue.

Step D: ({[(1Z)-2,2-Diethyl-1-oxidohydrazono]
amino}oxy)methyl 4-{1-[({2-chloro-5-[(2-methyl-2,3-dihydro-1H-indol-1-yl)carbamoyl]-
phenyl}sulphonyl)amino]ethyl}benzoate Dissolve the compound obtained in Step C ($7.07 \times 10^{-4}$ mol) in 1,4-dioxane (7 ml). Place the solution under stirring at ambient temperature and then add 15 ml of a 4N solution of HCl in 1,4-dioxane. The initially yellowish reaction mixture becomes darker and darker until it is virtually black. After stirring for 2 days at ambient temperature, the reaction mixture is evaporated to dryness under reduced pressure. The black residue obtained is chromatographed on a silica column using as eluant a 60/40 n-heptane/ethyl acetate mixture.

The title product is obtained in the form of a pale yellow meringue.

| Elemental microanalysis: | C | H | N | S |
|---|---|---|---|---|
| % theoretical: | 54.66 | 5.35 | 12.75 | 4.86 |
| % experimental: | 54.36 | 5.46 | 12.28 | 4.71 |

Pharmacological Study of the Products of the Invention

EXAMPLE A

Diuretic Effect

In Vivo

The diuretic effect is tested on conscious Wistar rats. The animals are subjected to fasting for 18 h before the experiment and put on a diet of water 90 minutes before the experiment. The product under test is then administered orally by force-feeding, the rat is placed in a metabolism cage and the volume of urine is measured after 6 hours. The volume is expressed in relation to the volume measured in a control group of rats.

Results: the increase in urine volume obtained using the products under test is greater than or equal to 20%.

By way of example, at an oral dose of 10 mg/kg the compounds of Examples 1 and 10 increase the excretion of urine by 108 and 248%, respectively.

EXAMPLE B

No-Donor Activity

In Vitro

Aorta rings without endothelium are used. After a first contraction induced by 60 mM KCl to characterise the sensitivity of the ring, and washing, a stable contraction is induced by noradrenaline (0.1-0.3 µM) in the presence or absence of ODQ. A cumulative concentration series is applied and the activity of the product under test is calculated by an $IC_{50}$ (dose that inhibits the maximum effect by 50%).

Results: the compounds according to the invention have a quite significant relaxant effect with $IC_{50}$ values of less than 1 µM.

By way of example, the compounds of Examples 1 and 10 have an $IC_{50}$ of 0.12 and 0.04 µM, respectively.

In Vivo

The NO-donor effect of the compound is evaluated by the reduction in pressure caused in SD rats anaesthetised with pentobarbital. After stabilisation of the arterial pressure, the product under test is administered i.v. in increasing doses.

Results: a reduction of the arterial pressure of at least 50% is observed with the compounds of the invention at doses less than or equal to 0.3 mg/kg.

By way of example, at an i.v. dose of 100 µg/kg the compounds of Examples 1 and 10 reduce the arterial pressure by 56 and 55%, respectively.

EXAMPLE C

Pharmaceutical Composition

Preparation formula for 1000 tablets each containing a dose of 100 mg of ({[(1Z)-2,2-diethyl-1-oxidohydrazono] amino}oxy)methyl 3-{[({2-chloro-5-[(2-methyl-5-nitro-2,3-dihydro-1H-indol-1-yl)carbamoyl]phenyl}sulphonyl) amino]methyl}benzoate

| (Example 1) | 100 g |
| Hydroxypropyl cellulose | 2 g |
| Wheat starch | 10 g |
| Lactose | 100 g |
| Magnesium stearate | 3 g |
| Talc | 3 g |

The invention claimed is:

1. A compound selected from those of formula (I):

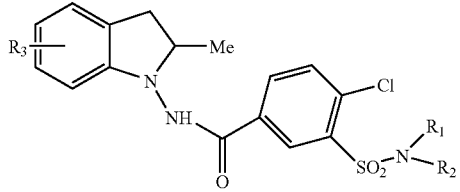

(I)

wherein:

$R_1$ represents a hydrogen atom or a —COOR group wherein R represents a linear or branched $(C_1-C_6)$alkyl group or an aryl-$(C_1-C_6)$alkyl group in which the alkyl moiety may be linear or branched;

$R_2$ represents a group G or a linear or branched $(C_1-C_6)$ alkyl group substituted by a group G, wherein G represents a —$(CH_2)_n$-A-$(CH_2)_m$—B—$(CR_4R_5)_p$—$(CH_2)_o$—$R_6$ group wherein:

n is 0, 1, 2 or 3, m is 0, 1, 2 or 3, p is 0 or 1, o is 0, 1 or 2, $R_4$ and $R_5$, which may be identical or different, each represent a hydrogen atom or a linear or branched $(C_1-C_6)$alkyl group, wherein one of the groups —$CH_2$— or —$CR_4R_5$— of the G chain may equally be replaced, if desired, by a phenylene, —PhC(O)— or —PhC(O)O— group, wherein Ph denotes phenyl, A and B, which may be identical or different, each represent a bond, a nitrogen atom or a group:

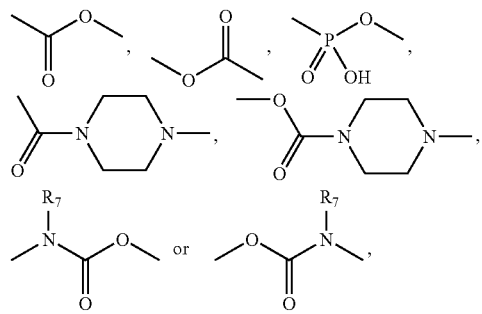

wherein $R_7$ represents a hydrogen atom or a linear or branched $(C_1-C_6)$alkyl group, and $R_6$ represents a group

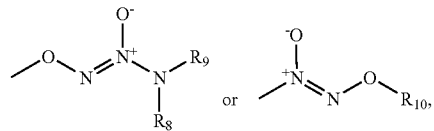

wherein $R_8$, $R_9$ and $R_{10}$, which may be identical or different, each represent a hydrogen atom or a linear or branched $(C_1-C_6)$alkyl group unsubstituted or substituted by an amino group, or $R_8$ and $R_9$ together form a linear or branched $(C_1-C_6)$alkylene chain; and $R_3$ represents a hydrogen atom, a linear or branched $(C_1-C_6)$alkyl group or an $NO_2$ group, its enantiomers, diastereoisomers, and addition salts thereof with a pharmaceutically acceptable acid or base.

2. The compound of claim 1, wherein $R_1$ represents a hydrogen atom.

3. The compounds of claim 1, wherein $R_3$ represents a hydrogen atom.

4. The compound of claim 1, wherein $R_3$ represents an $NO_2$ group.

5. The compound of claim 1, wherein $R_2$ represents a group:

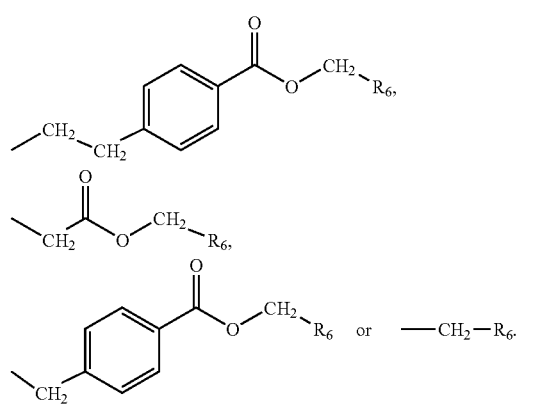

6. The compound of claim 1, wherein $R_6$ represents an —O—N=N(O)—$NR_8R_9$ group.

7. The compound of claim 1, wherein $R_8$ and $R_9$ represent a linear $(C_1$-$C_6)$alkyl group.

8. The compound of claim 1, which is selected from ({[(1Z)-2,2-diethyl-1-oxidohydrazono]amino}oxy)methyl 3-{[({2-chloro-5-[(2-methyl-5-nitro-2,3-dihydro-1H-indol-1-yl)carbamoyl]phenyl}sulphonyl)amino]methyl}benzoate, its enantiomers, diastereoisomers, and addition salts thereof with a pharmaceutically acceptable acid or base.

9. The compound of claim 1, which is selected from ({[(1Z)-2,2-diethyl-1-oxidohydrazono]amino}oxy)methyl 4-{[({2-chloro-5-[(2-methyl-2,3-dihydro-1H-indol-1-yl)carbamoyl]phenyl}sulphonyl)amino]methyl}benzoate, its enantiomers, diastereoisomers, and addition salts thereof with a pharmaceutically acceptable acid or base.

10. The compound of claim 1, which is selected from ({[(1Z)-2,2-diethyl-1-oxidohydrazono]amino}oxy)methyl 4-({[(2-chloro-5-{[(2R)-2-methyl-2,3-dihydro-1H-indol-1-yl]carbamoyl}phenyl)sulphonyl]amino}methyl)benzoate and addition salts thereof with a pharmaceutically acceptable acid or base.

11. The compound of claim 1, which is selected from ({[(1Z)-2,2-diethyl-1-oxidohydrazono]amino}oxy)methyl 4-{2-[({2-chloro-5-[(2-methyl-2,3-dihydro-1H-indol-1-yl)carbamoyl]phenyl}sulphonyl)amino]ethyl}benzoate, its enantiomers, diastereoisomers, and addition salts thereof with a pharmaceutically acceptable acid or base.

12. The compound of claim 1, which is selected from ({[(1Z)-2,2-diethyl-1-oxidohydrazono]amino oxy)methyl 4-{2-[({2-chloro-5-[((2R)-2-methyl-2,3-dihydro-1H-indol-1-yl)carbamoyl]phenyl}sulphonyl)amino]ethyl}benzoate and addition salts thereof with a pharmaceutically acceptable acid or base.

13. A pharmaceutical composition comprising as active ingredient a the compound of claim 1 in combination with one or more pharmaceutically acceptable, inert, non-toxic excipients or carriers.

14. A method for treating a condition selected from hypertension, retinopathy, cerebral accidents, dementia, left ventricular hypertrophy, cardiac insufficiency, angina pectoris, myocardial infarction, nephropathy cerebral and coronary accidents, arteritis vasculopathies, and hypertension of pulmonary, ocular or portal origin, such method comprising the step of administering to a living animal body, including a human, a therapeutically effective amount of a compound of claim 1.

* * * * *